(12) United States Patent
Afzali-Ardakani et al.

(10) Patent No.: US 10,578,577 B2
(45) Date of Patent: *Mar. 3, 2020

(54) METHODS OF FABRICATING AND OPERATING A SOLID-STATE ZINC SENSOR

(71) Applicant: INTERNATIONAL BUSINESS MACHINES CORPORATION, Armonk, NY (US)

(72) Inventors: Ali Afzali-Ardakani, Ossining, NY (US); Abram L. Falk, Port Chester, NY (US); Bharat Kumar, Tarrytown, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/635,447

(22) Filed: Jun. 28, 2017

(65) Prior Publication Data

US 2019/0004068 A1    Jan. 3, 2019

(51) Int. Cl.
| | | |
|---|---|---|
| *G01N 33/84* | (2006.01) | |
| *G01N 27/414* | (2006.01) | |
| *H01L 29/06* | (2006.01) | |
| *H01L 29/66* | (2006.01) | |
| *G01N 33/487* | (2006.01) | |

(52) U.S. Cl.
CPC ....... *G01N 27/414* (2013.01); *G01N 27/4146* (2013.01); *G01N 33/48714* (2013.01); *G01N 33/84* (2013.01); *H01L 29/0669* (2013.01); *H01L 29/66477* (2013.01); *G01N 2610/00* (2013.01); *G01N 2800/28* (2013.01)

(58) Field of Classification Search
None
See application file for complete search history.

(56) References Cited

U.S. PATENT DOCUMENTS

| | | | |
|---|---|---|---|
| 7,759,114 B2* | 7/2010 | Martin | G01N 33/54353 424/179.1 |
| 8,034,621 B2* | 10/2011 | Rao | C07D 401/14 436/80 |
| 8,530,183 B2 | 9/2013 | Li et al. | |
| 8,574,914 B2 | 11/2013 | Lippard et al. | |

(Continued)

OTHER PUBLICATIONS

Knopfmacher, O. et al. "Highly stable organic polymer field-effect transistor sensor for selective detection in the marine environment," Nature Communications 5:2954 (2014), including Supplementary information (Year: 2014).*

(Continued)

*Primary Examiner* — Christopher Adam Hixson
*Assistant Examiner* — Michelle Adams
(74) *Attorney, Agent, or Firm* — Cantor Colburn LLP; Vazken Alexanian

(57) ABSTRACT

Embodiments of the invention are directed to a solid-state zinc sensor. A non-limiting example of the sensor includes a semiconductor substrate. The sensor can also include an assembly surface on the semiconductor substrate. The sensor can also include a zinc detection monolayer chemically bound to the assembly surface. The sensor can also include a power supply electrically connected to the semiconductor substrate.

3 Claims, 5 Drawing Sheets

(56) References Cited

U.S. PATENT DOCUMENTS

| | | | |
|---|---|---|---|
| 9,110,014 | B2 | 8/2015 | Afzali-Ardakani et al. |
| 9,269,708 | B2 | 2/2016 | Rothberg et al. |
| 10,215,727 | B2 * | 2/2019 | Afzali-Ardakani ................ G01N 33/48714 |
| 2005/0142067 | A1 | 6/2005 | Frederickson et al. |
| 2015/0004711 | A1 | 1/2015 | Moore et al. |

OTHER PUBLICATIONS

Mittal, S.K. et al. "A Comparative Study of Linked 2, 2'-Dipyridylamine Ligand System as an Ion Selective Electrode for Ag (I) Ions," Int. J. Electrochem. Sci., 5 (2010) 1984-1995. (Year: 2010).*

Antonioli, B. et al. "Silver(I) complexation of linked 2,2'-dipyridylannine derivatives. Synthetic, solvent extraction, membrane transport and X-ray structural studies," Dalton Trans. Oct. 28, 2006; (40): 4783-4794. (Year: 2006).*

Minami, T. "A mercury(II) ion sensor device based on an organic field effect transistor with an extended-gate modified by dipicolylannine," Chem Commun. 2015; 51(100):17666-17668. (Year: 2015).*

Kwon et al., "Fluorescent Zinc Sensor with minimized Proton-Induced Interferences: Photophysical Mechanism for Fuorescence Turn-On Response and Detection of Endogenous Free Zinc Ions", Inorganic Chemistry; 2012, 51, pp. 8760-8774.

Woo et al., "Synthetic Control Over Photoinduced Electron Transfer in Phosphorescence Zinc Sensors" J. Am. Chem. Soc. 2013, 135, pp. 4771-4787.

Kwon et al., "Fluorescent Zinc Sensor with minimized Proton-Induced Interferences: Photophysical Mechanism for Fluorescence Turn-On Response and Detection of Endogenous Free Zinc Ions", Inorganic Chemistry; 2012, 51, pp. 3760-8774.

Afzali-Ardakani et al.; "Transistor-Based Zinc Sensor"; U.S. Appl. No. 15/801,392, filed Nov. 2, 2017.

List of IBM Patents or Patent Applications Treated as Related; Date Filed: Aug. 2, 2018, 2 pages.

Komatsu et al.; "Selective Zinc Sensor Molecules with Various Affinities for Zn2+, Revealing Dynamics and Regional Distribution of Synaptically Released Zn2+ in Hippocampal Slices"; J. Am. Chem. Soc.; vol. 127 No. 29; 2005; pp. 10197-10204.

Sudibya et al.; "Electrical Detection of Metal Ions Using Field-Effect Transistors Based on Micropatterned Reduced Graphene Oxide Films"; ACS Nano; vol. 5 No. 3; 2011; pp. 1990-1994.

Yang et al.; "Synthesis, Dual Fluorescence, and Fluoroionophoric Behavior of Dipyridylaminomethylstilbenes"; J. Org. Chem.; vol. 70 No. 15; 2005; pp. 6066-6073.

Zare-Dorabei et al.; "Highly efficient simultaneous ultrasonic-assisted adsorption of Pb(II), Cd(II), Ni(II) and Cu(II) ions from aqueous solutions by graphene oxide modified with 2, 2'-dipyridylamine: Central composite deisgn optimization," Ultrasonics Sonochemistry; vol. 32; 2016; pp. 265-276.

* cited by examiner

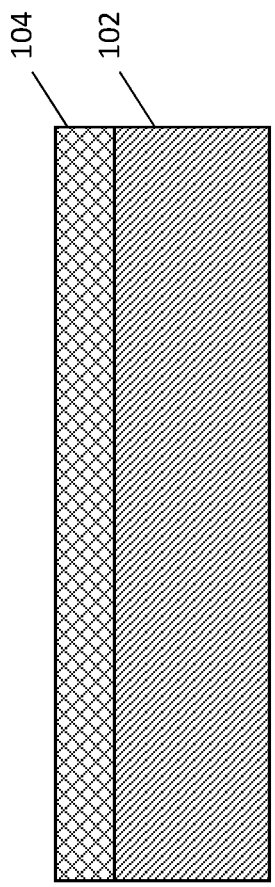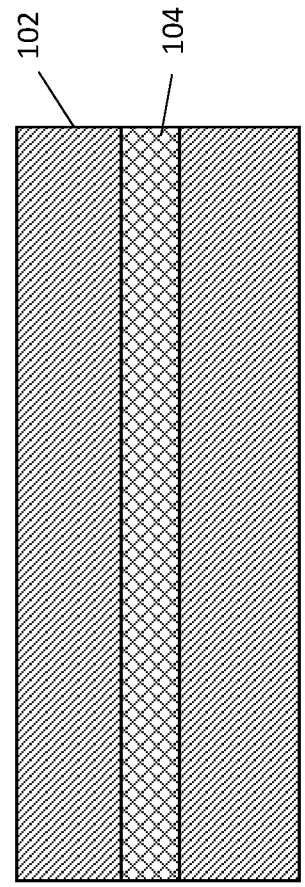
FIG. 2A
FIG. 2B

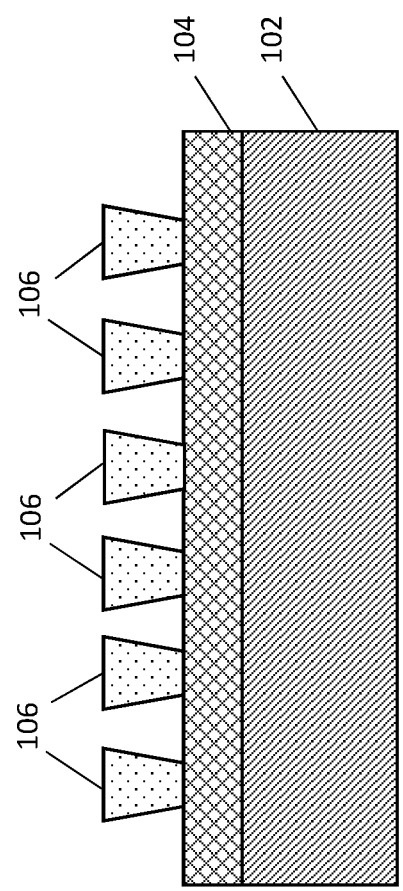

METHODS OF FABRICATING AND OPERATING A SOLID-STATE ZINC SENSOR

BACKGROUND

The present invention generally relates to fabrication methods and resulting structures for semiconductor devices. More specifically, the present invention relates to transistor-based (e.g., field effect transmitter (FET)-based) zinc sensors.

Zinc can play an important role in biological systems. In healthy individuals, zinc homeostasis is established and maintained for proper cellular functions. Disruptions or fluctuations in zinc levels in biological systems, however, can be correlated with a variety of neurological diseases and disorders. For instance, aberrant concentrations of zinc ions can be associated with Alzheimer's disease, amyotrophic lateral sclerosis (ALS), Parkinson's disease, ischemia, and epilepsy. Measuring and monitoring cellular zinc concentrations in biological systems can be useful in the treatment and study of such diseases and disorders.

SUMMARY

Embodiments of the invention are directed to a transistor-based zinc sensor. A non-limiting example of the sensor includes a semiconductor substrate. The sensor can also include an assembly surface on the semiconductor substrate. The sensor can also include a zinc detection monolayer chemically bound to the assembly surface. The sensor can also include a power supply electrically connected to the semiconductor substrate.

Embodiments of the present invention are directed to a method for fabricating a solid-state zinc sensor. A non-limiting example of the method includes forming an assembly surface on a semiconductor substrate of a semiconductor system. The method can also include attaching a zinc detection monolayer to the assembly surface. The method can also include connecting a power supply to the semiconductor system. The method can also include connecting a current detector to the assembly surface.

Embodiments of the present invention are directed to a method of operating a solid-state zinc sensor. A non-limiting example of operating the method includes attaching a zinc detection monolayer to an assembly surface of a semiconductor system, wherein the semiconductor system includes a source, a drain, and a gate. The method can also include applying a source-drain bias to the semiconductor system. The method can also include measuring a first drain current. The method can also include exposing the zinc detection monolayer to a biological fluid. The method can also include measuring a second drain current. The method can also include determining a zinc concentration of biological fluid based at least in part upon the first drain current and the second drain current.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 2A depicts a cross-sectional side view of a zinc sensor after a fabrication operation according to embodiments of the invention;

FIG. 2B depicts a top-down view of a zinc sensor after a fabrication operation according to embodiments of the invention;

FIG. 2C depicts a cross-sectional side view of a zinc sensor after another fabrication operation according to embodiments of the invention;

Figure 1:
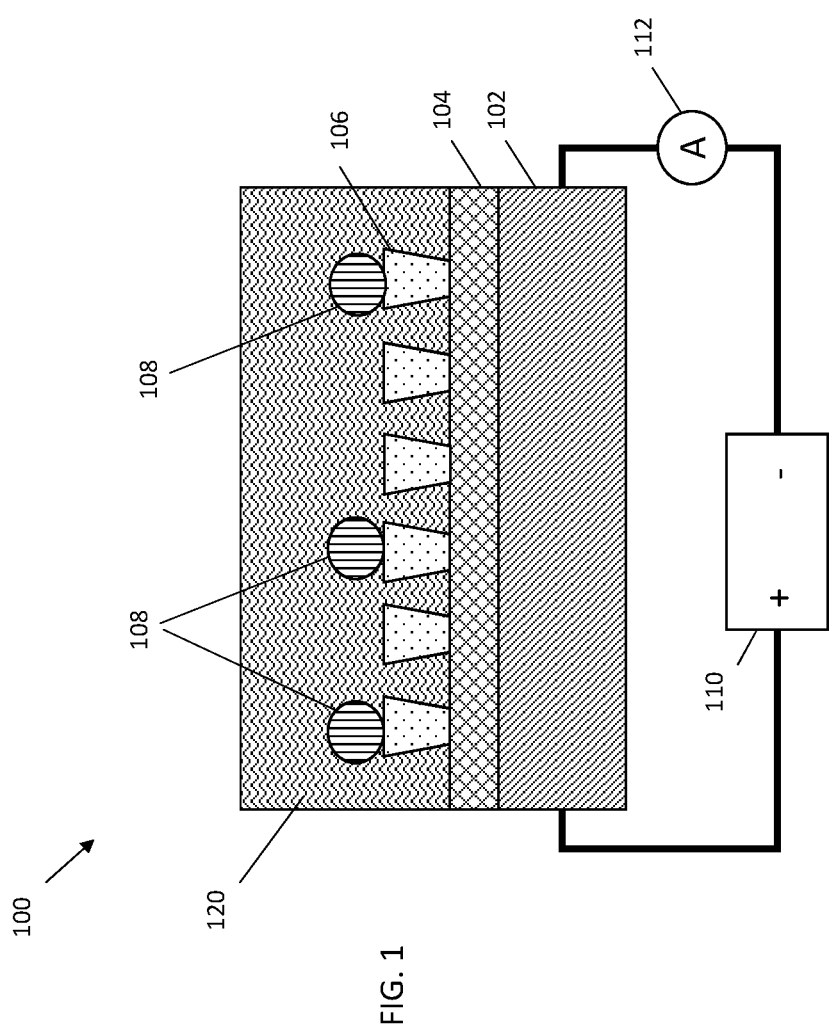
FIG. 1 depicts a zinc sensor system according to embodiments of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments of the invention, the various elements illustrated in the figures are provided with two or three digit reference numbers. With minor exceptions, the leftmost digit(s) of each reference number correspond to the figure in which its element is first illustrated.

DETAILED DESCRIPTION

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the invention, zinc is an important mineral for a variety of biological functions and is present in high levels in the brain. Zinc homeostasis includes maintaining a constant biological state of zinc. The homeostasis of free zinc ions, and related impairments, have been directly linked to a variety of neurological diseases and conditions, such as Alzheimer's, ALS, Parkinson's disease, ischemia, and epilepsy. Investigation of zinc homeostasis, therefore, can be a critical component of research and treatment of such conditions.

Conventional measurement of zinc ions using optical methods can require cumbersome equipment or off-site measurement. The ability to provide on-site, sensitive results in studies of zinc concentration and concentration changes is desirable in biological applications, which can involve relatively small changes in concentration over a short period of time.

Turning now to an overview of the aspects of the invention, one or more embodiments of the invention provide a solid state, transistor-based non-optical zinc sensor for determination of zinc concentration in biological fluids. Embodiments of the present invention include a FET-based sensor with a functionalized surface capable of binding zinc ions. Upon binding zinc ions, sensors according to embodiments of the invention can experience a change in electrical output relative to the electrical output of a surface free of zinc ions directly proportional to bound ion concentration.

The above-described aspects of the invention can allow sensitive, on-site measurement of zinc concentrations in biological fluid for analysis, study, and treatment of neurological conditions implicating zinc homeostasis by providing a portable, transistor-based zinc sensor that is light weight and cost effective. Embodiments of the invention can provide sensitive zinc measurements without the need for heavy or specialized equipment by using a transistor-based system that does not require optical components for ionic detection. Embodiments of the invention can leverage changes in electrical properties of a transistor-based system upon binding of a positively charged zinc ion to determine zinc concentrations in biological fluid.

Turning now to a more detailed description of aspects of the present invention, FIG. 1 depicts a cross-sectional side view of an exemplary transistor-based zinc sensor 100 according to embodiments of the invention. The sensor 100 can include an assembly surface 104 and a semiconductor substrate 102. The substrate 102 can be a substrate of a field effect transistor. The sensor 100 can also include a zinc detection monolayer 106. The zinc detection monolayer 106 can be chemically bound to the assembly surface 104. In some embodiments of the invention, the zinc detection monolayer 106 is chemically selective to zinc ions. The sensor 100 can also include a power supply 110 electrically connected to the system 100, for example to the semiconductor substrate. In some embodiments of the invention, a power supply 110 is electrically connected to a source and drain of a FET-based transistor. In some embodiments of the invention, the system 100 includes a current detector or voltage detector 112. In operation, the system 100 can be placed in contact with a biological fluid 120. The biological fluid 120 can include zinc ions ($Zn^{2+}$) 108.

In some embodiments of the invention, the semiconductor substrate 102 includes silicon. In some embodiments of the invention, the semiconductor substrate includes a semiconductor on insulator (SOI) wafer. An SOI wafer can include a thin layer of a semiconducting material atop an insulating layer (e.g., an oxide layer) which is in turn disposed on a silicon substrate. The semiconducting material can include, but is not limited to, Si (silicon), strained Si, SiC (silicon carbide), Ge (geranium), SiGe (silicon germanium), SiGeC (silicon-germanium-carbon), Si alloys, Ge alloys, GaAs (gallium arsenide), InAs (indium arsenide), InP (indium phosphide), or any combination thereof. In some embodiments of the invention, the semiconductor substrate 102 includes carbon nanotubes, such as a thin layer of carbon nanotubes atop a silicon substrate or atop an insulating layer of an SOI wafer. In some embodiments of the invention, the semiconductor substrate 102 includes silicon or carbon nanotubes as channel material.

Assembly surface 104 can include, for example, a dielectric layer of a FET-based transistor. In some embodiments of the invention, assembly surface 104 includes an oxide layer, such as silicon dioxide, tetraethylorthosilicate (TEOS) oxide, high aspect ratio plasma (HARP) oxide, high temperature oxide (HTO), high density plasma (HDP) oxide, oxides (e.g., silicon oxides) formed by an atomic layer deposition (ALD) process, or any combination thereof. In some embodiments of the invention, assembly surface 104 includes a metal oxide, such as an oxide of hafnium (Hf), aluminum (Al), tungsten (W), or titanium (Ti). In some embodiments of the invention, the assembly surface 104 includes silicon dioxide ($SiO_2$) or a silicon group such as bare silicon with Si—H bonds on the surface for functionalization or for example amorphous hydrogenated silicon (Si—H).

Zinc detection monolayer 106 can form a sensing surface of the system 100. The zinc detection monolayer 106 can include, for example, a monolayer selectively formed on metal oxides, such as $HfO_2$ or $Al_2O_3$ of an assembly surface 104. In some embodiments of the invention, zinc detection monolayer 106 includes a compound capable of binding zinc ions, such as di-picolylamine or derivatives thereof. Di-picolylamine, for example, is known to bind to free zinc ions and can be attached to an assembly surface 104, for example, through a hydroxamic acid group. In operation, when zinc ions bind to the zinc detection monolayer 106, the electrical properties, such as a system current, can change, for instance due to the association of added positive charge to the system from the zinc ions.

The zinc detection monolayer 106 can be self-assembled onto the assembly surface 104 of a standard FET device, for instance, after cleaning the assembly surface 104. The modified surface can be placed in a solution containing free zinc ions, such as a biological fluid, and electrical data can be recorded before and after adding zinc ions. In some embodiments of the invention, the biological fluid is brain fluid. Complexation of zinc ion with picolylamine can change the surface charge of the assembly surface 104 and can result in a change in electrical output that is directly proportional to the concentration of free zinc ions.

In some embodiments of the invention, the zinc detection monolayer includes a compound of the following formula:

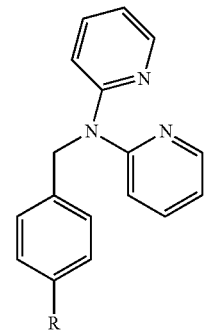

wherein N is nitrogen and R includes an acid, an ether, an alcohol, an alkene, an alkane, or a silicon group.

FIGS. 2A-2C depict a schematic illustrating an exemplary method of fabricating a solid-state zinc sensor according to one or more embodiments of the present invention. FIG. 2A illustrates a cross-sectional side view of an exemplary semiconductor substrate 102 including an assembly surface 104 according to one or more embodiments of the present invention. The assembly surface, for example, can be, for example, a nanowire deposited on the surface of the semiconductor substrate. FIG. 2B illustrates a top-down view of the exemplary semiconductor substrate 102 and assembly surface 104 shown in FIG. 2A.

As is illustrated in FIG. 2C, the assembly surface 104 can be functionalized with a zinc detection monolayer 106. In some embodiments of the invention, when the assembly surface 104 includes a metal-oxide surface, a zinc detection monolayer can be formed from a reaction between the surface with a compound of formula (I)

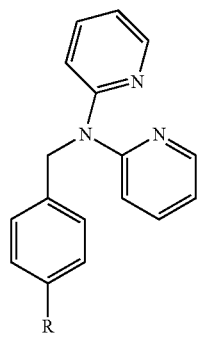

(I)

wherein N is nitrogen and R is CONHOH or POSH. In some embodiments of the invention, when the assembly surface 104 includes a silicon dioxide surface, a zinc detection monolayer can be formed from a reaction between the surface with a compound of formula (I) above, wherein R is $Si(OCH_2CH_3)_2$, $SiCl(OCH_2CH_3)$, or $SiCl_3$. In such embodiments of the invention, for example, the zinc detection monolayer can be prepared in one step starting from a compound in which R is Cl using a metal halogen exchange according to methods known to those skilled in the art. In some embodiments of the invention, when the assembly surface 104 includes a surface including bare silicon with Si—H bonds on the surface, a zinc detection monolayer can be formed from a reaction between the surface with a compound of formula (I) above, wherein R is —C≡C, —OH, or CCH.

Figure 3:
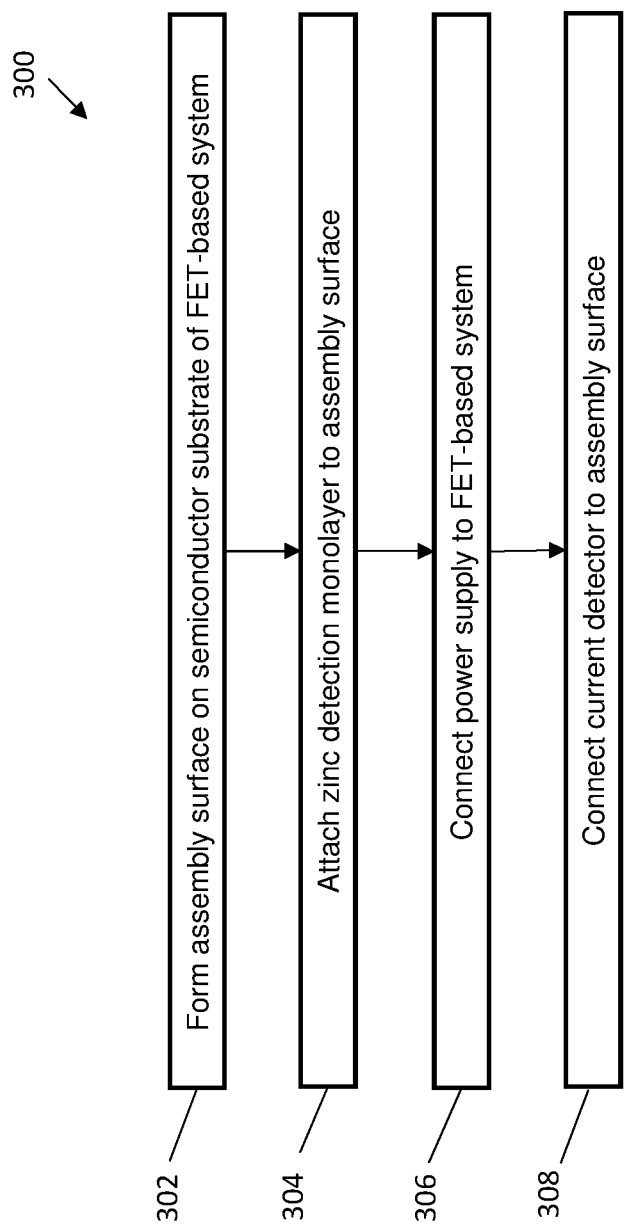
FIG. 3 depicts a flow diagram illustrating a method according to one or more embodiments of the invention.

FIG. 3 depicts a flow diagram of an exemplary method 300 of fabricating a solid-state zinc sensor according to one or more embodiments of the present invention. The method 300 can include, as shown at block 302, forming an assembly surface on a semiconductor substrate of a FET-based system. The FET-based system can include a semiconductor system including a source, drain, and gate, for example. The method 300 can also include, as shown at block 304, attaching a zinc detection monolayer to the assembly surface. The method 300 can also include, as shown at block 306, connecting a power supply to the FET-based system. The method 300 can also include, as shown at block 308, connecting a current detector to the assembly surface.

Figure 4:
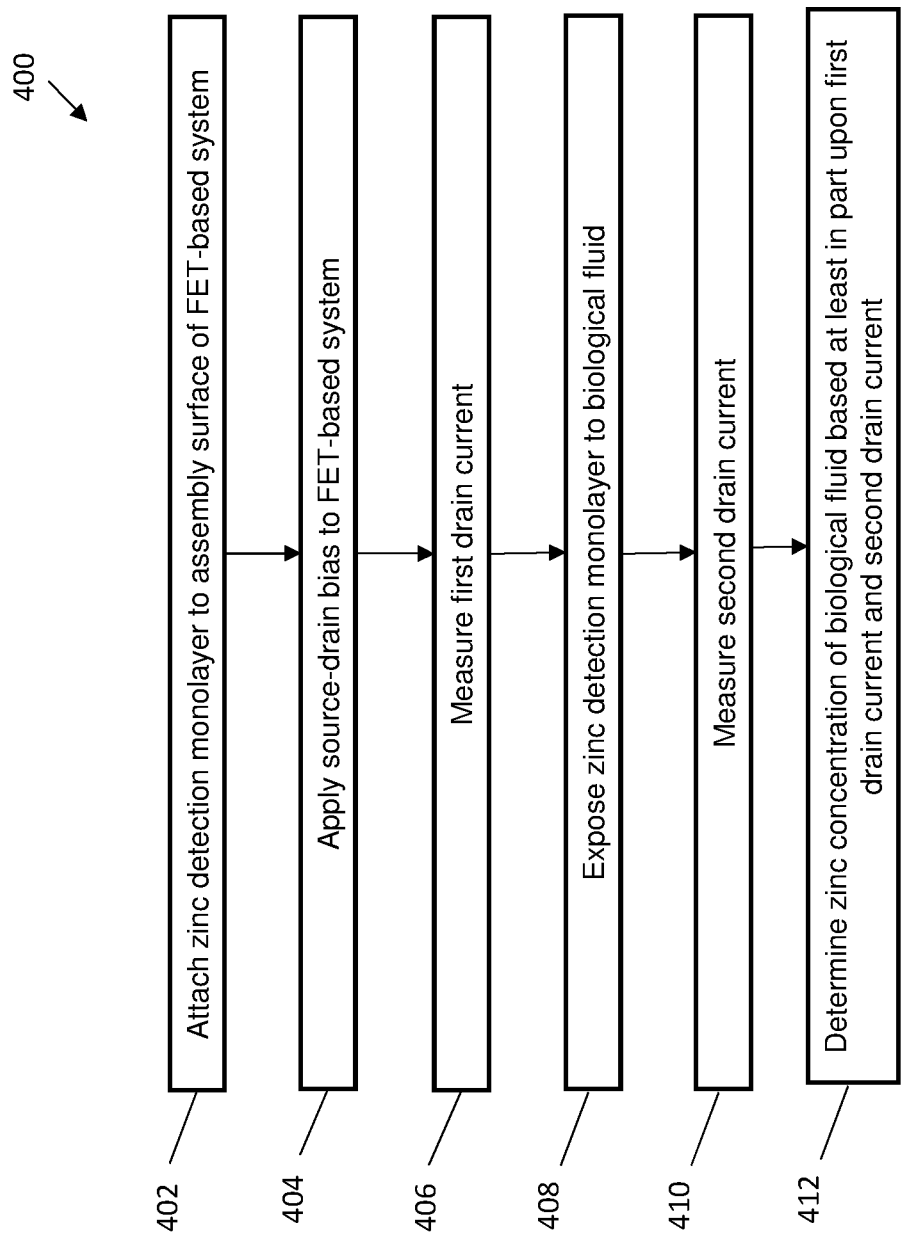
FIG. 4 depicts a flow diagram illustrating a method according to one or more embodiments of the invention.

FIG. 4 depicts a flow diagram of an exemplary method 400 of operating a solid-state zinc sensor according to one or more embodiments of the present invention. The method 400 can include, as shown at block 402, attaching a zinc detection monolayer to an assembly surface of a semiconductor system, wherein the semiconductor system includes a source, a drain, and a gate. The method 400 can also include, as shown at block 404, applying a source-drain bias to the semiconductor system. The method 400 can also include, as shown at block 406, measuring a first drain current. The first drain current, for instance, can include a drain current when a source-drain bias is applied before exposure to a fluid containing zinc. The method 400 can also include, as shown at block 408, exposing the zinc detection monolayer to a fluid, such as a biological fluid. The method 400 can also include, as shown at block 410, measuring a second drain current. The second drain current, for instance, can include a drain current when a source drain bias is applied after or during exposure to the biological fluid. The method 400 can also include, as shown at block 412, determining a zinc concentration of biological fluid based at least in part upon the first drain current and the second drain current.

In some embodiments of the invention, changes in output current can easily detect zinc ions in biological solutions. Desirably, zinc ion concentrations can conveniently be measured on-site without the need for optical systems or specialized or heavy equipment.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The phrase "selective to," such as, for example, "a first element selective to a second element," means that the first element can be etched and the second element can act as an etch stop.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention, the practical application or technical improvement over technologies found in the marketplace, or to enable others of ordinary skill in the art to understand the embodiments described herein.

What is claimed is:

1. A solid-state zinc sensor comprising:
    a semiconductor substrate;
    an assembly surface comprising a metal oxide layer on the semiconductor substrate;
    a zinc detection monolayer chemically bound to the assembly surface, said zinc detection monolayer formed by reacting the assembly surface with a compound of the formula:

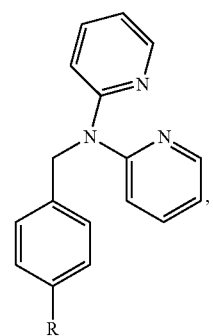

where R is CONHOH or POSH; and
a power supply electrically connected to the semiconductor substrate.

2. The sensor of claim 1, wherein the semiconductor substrate comprises silicon.

3. The sensor of claim 1, wherein the metal oxide layer comprises hafnium oxide, aluminum oxide, tungsten oxide, or titanium oxide.

\* \* \* \* \*